(12) United States Patent
Lee et al.

(10) Patent No.: US 9,010,173 B2
(45) Date of Patent: Apr. 21, 2015

(54) POLLUTION MEASUREMENT APPARATUS FOR EASILY EXCHANGING SENSOR

(71) Applicant: Scientec Lab Center Co., Ltd., Daejeon (KR)

(72) Inventors: Ik-Jae Lee, Daejeon (KR); Han-Soo Kim, Daejeon (KR); Chang-Ik Kang, Daejeon (KR); Ji-Sun Kim, Daejeon (KR); Sun-Tae Kim, Daejeon (KR)

(73) Assignee: Scientec Lab Center Co., Ltd., Daejeon (KR)

( * ) Notice: Subject to any disclaimer, the term of this patent is extended or adjusted under 35 U.S.C. 154(b) by 333 days.

(21) Appl. No.: 13/645,828

(22) Filed: Oct. 5, 2012

(65) Prior Publication Data

US 2013/0145824 A1 Jun. 13, 2013

(30) Foreign Application Priority Data

Dec. 9, 2011 (KR) ........................ 10-2011-0132138

(51) Int. Cl.
*G01N 33/00* (2006.01)
*G01D 11/30* (2006.01)

(52) U.S. Cl.
CPC ............ *G01D 11/30* (2013.01); *G01N 33/0032* (2013.01)

(58) Field of Classification Search
USPC ............................................. 73/31.02, 31.03
See application file for complete search history.

(56) References Cited

U.S. PATENT DOCUMENTS 5,746,976 A * 5/1998 Yamada et al. ................. 422/62
8,196,479 B2 * 6/2012 Ludwick et al. ........... 73/863.31

FOREIGN PATENT DOCUMENTS

JP         08170943 A     7/1996
KR   10-2008-0034425 A     4/2008
KR   10-2011-0043838 A     4/2011

* cited by examiner

*Primary Examiner* — Hezron E Williams
*Assistant Examiner* — Mark A Shabman
(74) *Attorney, Agent, or Firm* — Sherr & Jiang, PLLC (57) ABSTRACT

Disclosed is a pollution measurement apparatus which measures a pollutant concentration and a pollutant component in gas, and more particularly a pollution measurement apparatus for easily exchanging a sensor, which can facilely exchange only desired sensors when it is required to exchange part of multiple sensors for sensing pollution.

8 Claims, 10 Drawing Sheets

POLLUTION MEASUREMENT APPARATUS FOR EASILY EXCHANGING SENSOR

CROSS-REFERENCE(S) TO RELATED APPLICATIONS

The present invention claims priority of Korean Patent Application No. 10-2011-0132138, filed on Dec. 9, 2011, which is incorporated herein by reference.

BACKGROUND OF THE INVENTION

1. Field of the Invention

The present invention relates to a pollution measurement apparatus which measures a pollutant concentration and a pollutant component in gas, and more particularly to a pollution measurement apparatus for easily exchanging a sensor, which can facilely exchange only desired sensors when it is required to exchange part of multiple sensors for sensing pollution.

2. Description of Related Art

In order to measure a pollutant concentration and a pollutant component in gas, there has been disclosed a method for measuring concentration of gas and device for the same (Korean Patent Application No. 10-2009-0100544), which is filed on Oct. 22, 2009.

However, in the device disclosed in the "method for measuring concentration of gas and device for the same (Korean Patent Application No. 10-2009-0100544)", since a plurality of sensors for measuring a pollutant concentration and a pollutant component in gas are disposed on an integrally formed single passage so as to form a single sensing part, there is a problem that, when it is necessary to exchange one of the plurality of sensors, the entire sensing part has to be separated from the device.

SUMMARY OF THE INVENTION

An embodiment of the present invention is directed to providing a pollution measurement apparatus in which, when it is required to exchange a specific gas concentration measuring sensor or a main operation part, a measurement unit having the specific gas concentration measuring sensor or main operation part is separated from a receiving portion of a main body and then exchanged with other equivalent measurement unit, thereby facilitating sensor exchange.

To achieve the object of the present invention, the present invention provides a pollution measurement apparatus for easily exchanging a sensor, comprising: a main block 120 in which a main passage 120H is formed and also a gas concentration measuring sensor 220S contacted with gas flowed in the main passage 120H is installed; a main case 420 in which the main block 120 and a main operation part 520 connected with the gas concentration measuring sensor 220S are installed; a main inlet pipe 321 which is protruded toward a rear side of the main case 420 so as to be communicated with the main passage 120H; a main outlet pipe 323 which is protruded toward the rear side of the main case 420 so as to be communicated with the main passage 120H; a main body 1000 which is formed with a receiving portion that n main cases 420 are fitted therein through a front surface thereof; and a k-th main connecting means which connects and communicates the main outlet pipe 323 protruded toward a rear side of a k-th main case 420-k out of the n main cases 420 and the main inlet pipe 321 protruded toward a rear side of a (k+1)-th main case 420-(k+1) out of the n main cases 420 with each other, wherein n is a natural number more than 2 and k is a natural number from 1 to n-1.

Preferably, the rear surface of the main body 1000 is formed with n-1 main flow grooves 1220G, and a k-th main flow groove 1220G-k out of the n-1 main flow grooves 1220G is formed with a k-th main outlet hole 1220H3-k in which the main outlet pipe 323 protruded toward a rear side of a k-th main case 420-k is inserted so as to be communicated with a k-th main flow groove 1220G-k and a k-th main inlet hole 1220H1-k in which the main inlet pipe 321 protruded toward a rear side of a (k+1)-th main case 420-(k+1) is inserted so as to be communicated with the k-th main flow groove 1220G-k, and the k-th main connecting means includes a k-th main cover plate which is installed at the rear surface of the main body 1000 so as to air-tightly close an opening end of the k-th main flow groove 1220G-k.

Preferably, the pollution measurement apparatus further includes a first sub-case 410 which is fitted into the receiving portion of the main body 1000 and in which a 1-1st sub-inlet pipe 311-1 for injecting odorless air, a 1-2nd sub-inlet pipe 311-2 for injecting polluted gas and a first sub-outlet pipe 313 are respectively protruded backward, and a choice valve is installed so as to selectively connect one of the 1-1st sub-inlet pipe 311-1 and the 1-2nd sub-inlet pipe 311-2 with the first sub-outlet pipe 313; and a first sub-connecting means which communicates and connects the first sub-outlet pipe 313 with the main inlet pipe 321 protruded toward a rear side of a first main case 420-1 out of the n main cases 420.

Preferably, a first sub-flow groove 1210G through which the gas is flowed is formed in the rear surface of the main body 1000, and the first sub-flow groove 1210G is formed with a first sub-outlet hole 1210H3 in which the first sub-outlet pipe 313 is inserted so as to be communicated with the first sub-flow groove 1210G, and a first sub-inlet hole 1210H1 in which the main inlet pipe 321 protruded toward the rear side of the first main case 420-1 is inserted so as to be communicated with the first sub-flow groove 1210G, and the first sub-connecting means includes a first sub-cover plate which is installed at the rear surface of the main body 1000 so as to air-tightly close an opening end of the first sub-flow groove 1210G.

Preferably, the pollution measurement apparatus further includes a sub-block 130 in which a sub-passage 130H is formed, and a physical property measuring sensor 230S for sensing at least one of temperature and humidity of the gas flowed in the sub-passage 130H is installed; a second sub-case 430 which is fitted into the receiving portion of the main body 1000 and in which the sub-block 130 and a sub-operation part 530 connected with the physical property measuring sensor 230S are installed; a second sub-inlet pipe 331 which is protruded toward a rear side of the sub-case 430 so as to be communicated with the sub-passage 130H; a second sub-outlet pipe 333 which is protruded toward the rear side of the sub-case 430 so as to be communicated with the sub-passage 130H; and a second sub-connecting means which communicates and connects the second sub-inlet pipe 331 with the main outlet pipe 323 protruded toward a rear side of an n-th main case 420-n out of the n main cases 420.

Preferably, a second sub-flow groove 1230G through which the gas is flowed is formed in the rear surface of the main body 1000, and the second sub-flow groove 1230G is formed with a second sub-outlet hole 1230H3 in which the main outlet pipe 323 protruded toward the rear side of the n-th main case 420-n is inserted so as to be communicated with the second sub-flow groove 1230G, and a second sub-inlet hole 1230H1 in which the second sub-inlet pipe 331 is inserted so as to be communicated with the second sub-flow groove 1230G, and the second sub-connecting means comprises a second sub-cover plate which is installed at the rear surface of the main body 1000 so as to air-tightly close an opening end of the second sub-flow groove 1230G.

Preferably, the rear surface of the main body 1000 is formed with a 1-1st main body inlet hole 1111H1 in which the 1-1st sub-inlet pipe 311-1 is inserted and a 1-2nd main body inlet hole 1112H1 in which the 1-2nd sub-inlet pipe 311-2 is inserted.

Preferably, the rear surface of the main body 1000 is formed with a main body outlet hole 1300H3 in which the second sub-outlet pipe 333 is inserted.

Preferably, a display part 1500 for displaying a concentration of a pollutant component is installed at the main body 1000, and a main display part connector 1520C connected with the display part 1500 is installed in the receiving part of the main body 1000, and the main operation part 520 is provided with a main operation part connector 520C which is fitted into the main display part connector 1520C when the main case 420 is fitted into the receiving portion of the main body 1000.

[Detailed Description of Main Elements]

| | |
|---|---|
| 120: main block | 120H: main passage |
| 130: sub-block | 130H: sub-passage |
| 220S: gas concentration measuring sensor | |
| 230S: physical property measuring sensor | |
| 311-1: 1-1st sub-inlet pipe | 311-2: 1-2st sub-inlet pipe |
| 313: first sub-outlet pipe | |
| 321: main inlet pipe | 323: main outlet pipe |
| 331: second sub-inlet pipe | 333: second sub-outlet pipe |
| 410: first sub-case | 420: main case |
| 420-1: first main case | 420-k: k-th main case |
| 420-(k + 1): (k + 1)-th main case | |
| 420-n: n-th main case | 430: second sub-case |
| 520: main operation part | |
| 520C: main operation part connector | |
| 530: sub-operation part | 1000: main body |
| 1111H1: 1-1st main body inlet hole | |
| 1112H1: 1-2nd main body inlet hole | |
| 1210G: first sub-flow groove | |
| 1210H1: first sub-inlet hole | |
| 1210H3: first sub-outlet hole | |
| 1220G: main flow groove | |
| 1220G-k: k-th main flow groove | |
| 1220H1-k: k-th main inlet hole | |
| 1220H3-k: k-th main outlet hole | |
| 1230G: second sub-flow groove | |

-continued

[Detailed Description of Main Elements]

| | |
|---|---|
| 1230H1: second sub-inlet hole | |
| 1230H3: second sub-outlet hole | |
| 1300H3: main body outlet hole | 1500: display part |
| 1520C: main display part connector | |
| CV: choice valve | |

DESCRIPTION OF SPECIFIC EMBODIMENTS

Hereinafter, the embodiments of the present invention will be described in detail with reference to accompanying drawings.

Figure 1:
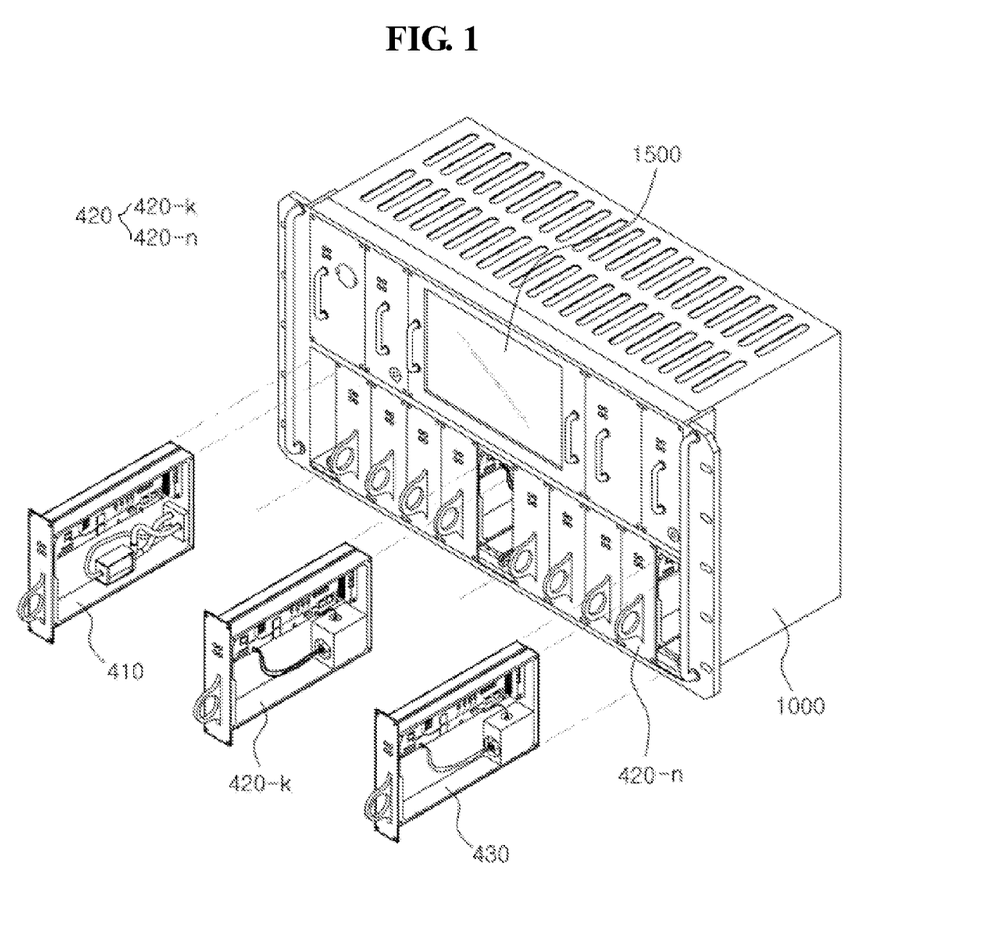
FIG. 1 is a front perspective view of an embodiment of the present invention.
Figure 2:
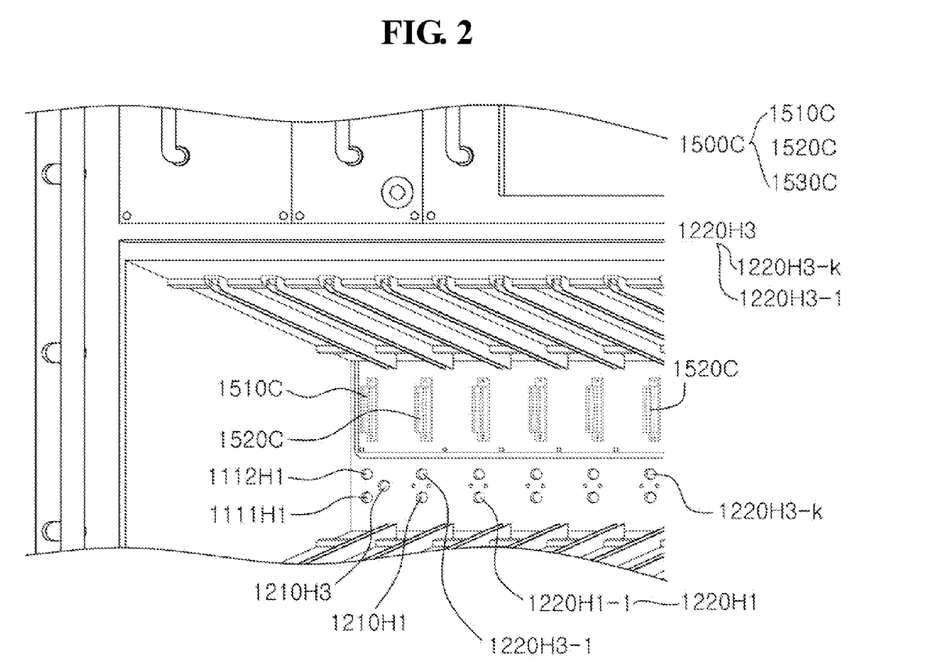
FIGS. 2 and 3 are perspective views of a receiving portion formed at a lower portion of a main body of FIG. 1.
Figure 3:
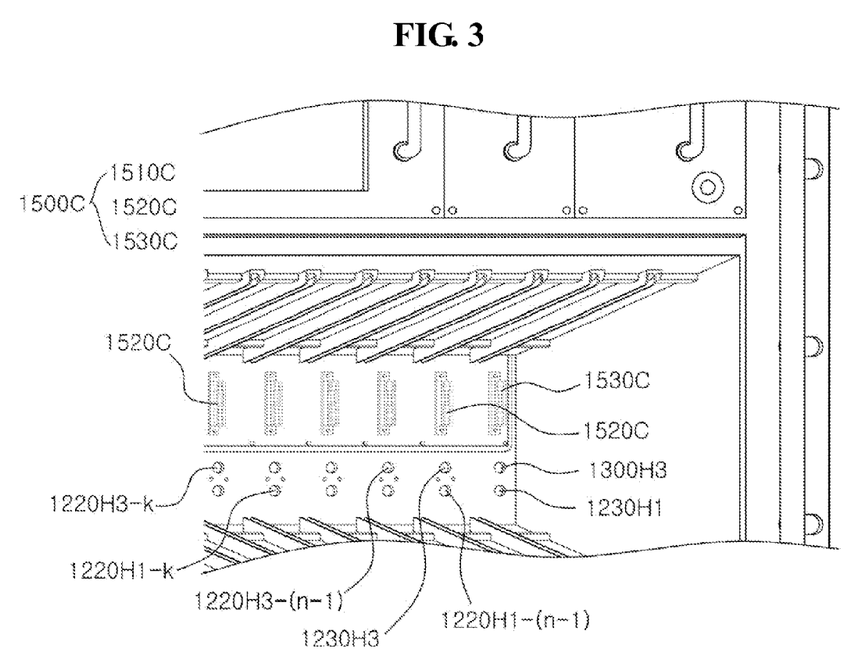
Figure 4:
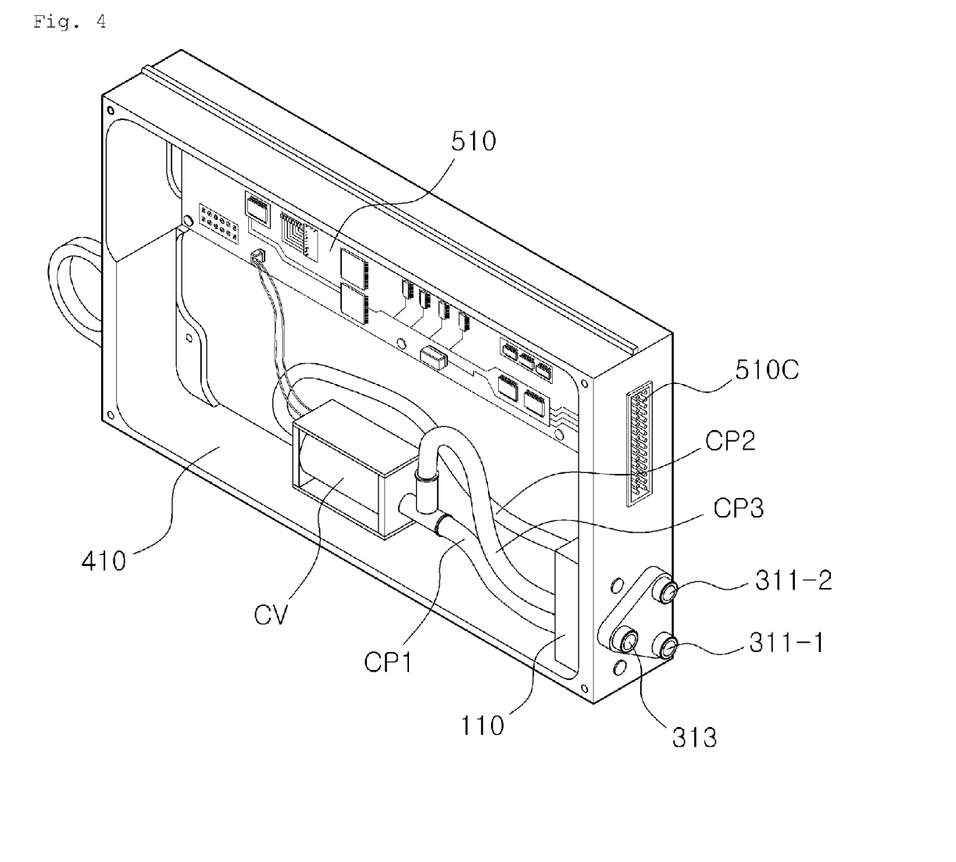
FIG. 4 is a perspective view of a first sub-case fitted into the receiving portion of FIG. 3.
Figure 5:
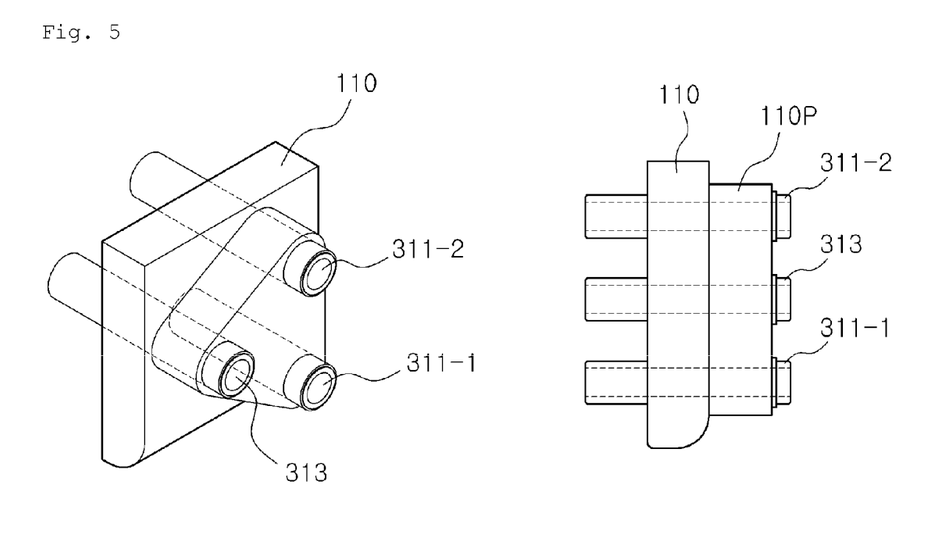
FIG. 5 is a perspective view and a side view of a supporting block installed at the first sub-case of FIG. 4.
Figure 6:
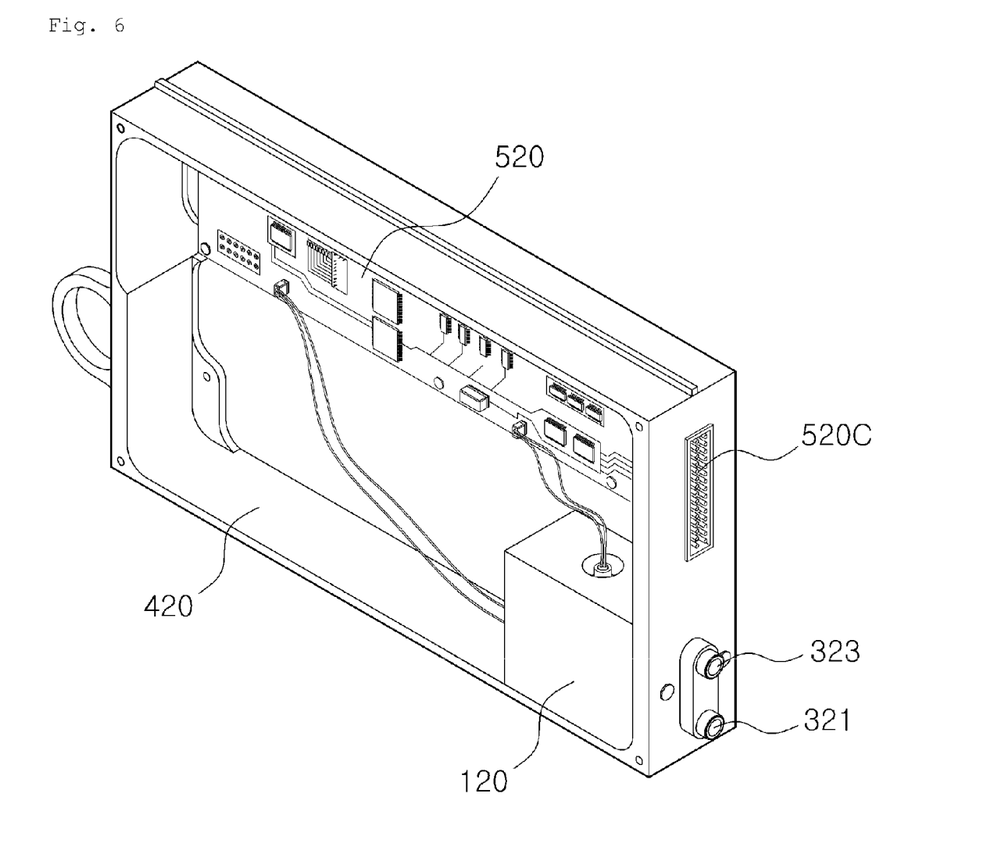
FIG. 6 is a perspective view of a main case fitted into the receiving portion of FIG. 3.
Figure 7:
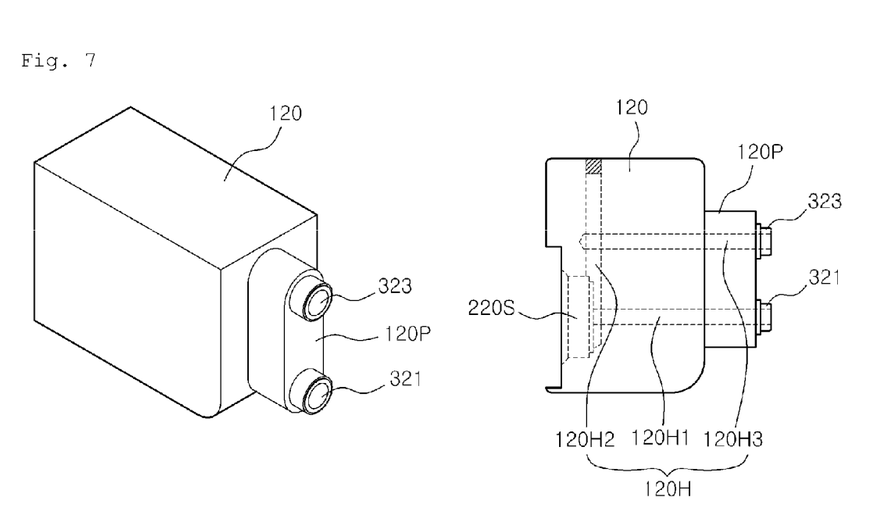
FIG. 7 is a perspective view and a side view of a main block installed at the main case of FIG. 6.
Figure 8:
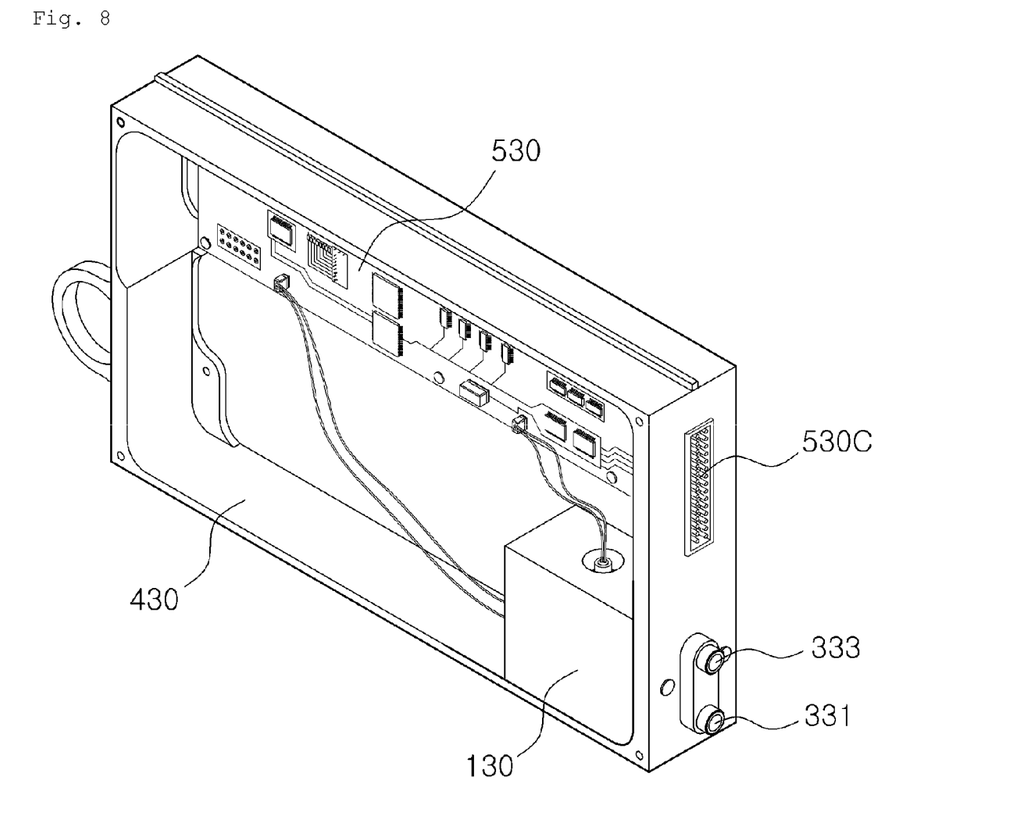
FIG. 8 is a perspective view of a second sub-case fitted into the receiving portion of FIG. 3.
Figure 9:
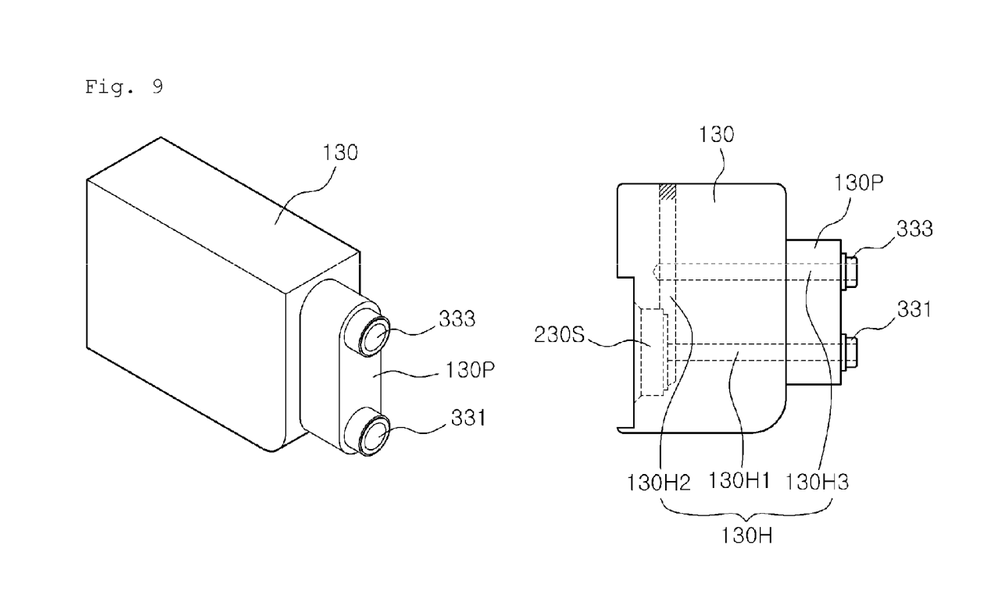
FIG. 9 is a perspective view and a side view of a sub block installed at the second sub-case of FIG. 8.
Figure 10:
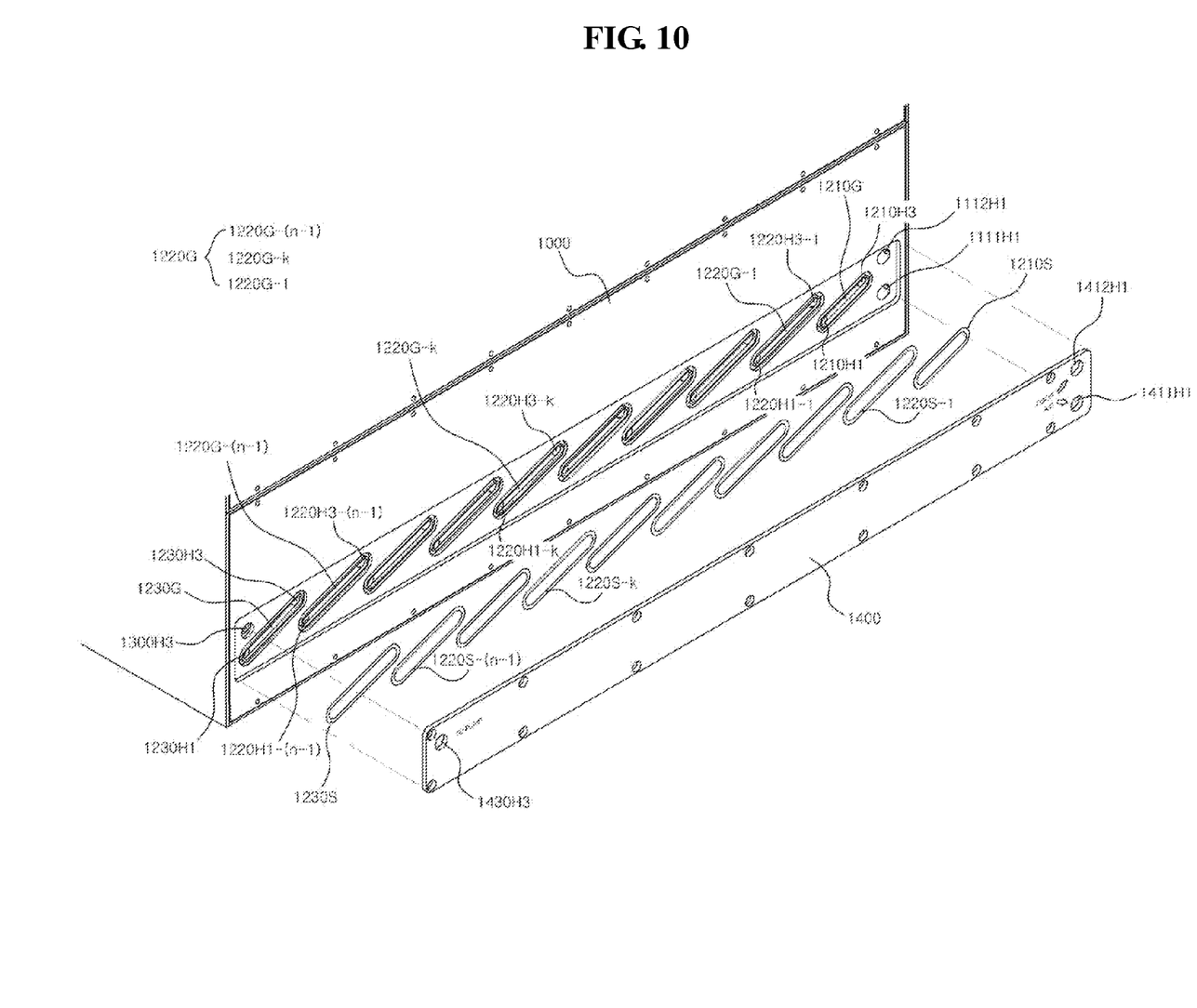
FIG. 10 is a schematic rear perspective view of the embodiment of the present invention.

FIG. 1 is a front perspective view of an embodiment of the present invention, FIGS. 2 and 3 are perspective views of a receiving portion formed at a lower portion of a main body of FIG. 1, FIG. 4 is a perspective view of a first sub-case fitted into the receiving portion of FIG. 3, FIG. 5 is a perspective view and a side view of a supporting block installed at the first sub-case of FIG. 4, FIG. 6 is a perspective view of a main case fitted into the receiving portion of FIG. 3, FIG. 7 is a perspective view and a side view of a main block installed at the main case of FIG. 6, FIG. 8 is a perspective view of a second sub-case fitted into the receiving portion of FIG. 3, FIG. 9 is a perspective view and a side view of a sub block installed at the second sub-case of FIG. 8, and FIG. 10 is a schematic rear perspective view of the embodiment of the present invention.

Referring to FIGS. 1 to 3, an embodiment of the present invention includes a main body 1000. A first sub-case 410, n main cases 420 and a second sub-case 430 are fitted into a lower portion of the main body 1000. Therefore, a receiving portion (not designated by a reference numeral) for receiving the first sub-case 410, the n main cases 420 and the second sub-case 430 is formed in a front surface of the main body 1000. A plurality of rails (not designated by a reference numeral) may be installed in the receiving portion (not designated by a reference numeral) of the main body 1000 so that the first sub-case 410, the n main cases 420 and the second sub-case 430 can be facilely fitted into the receiving portion (not designated by a reference numeral) of the main body 1000. Herein, n is a natural number. The drawings show a case that n is 9.

Referring to FIG. 4, a supporting block 110, a choice valve CV and a valve controller 510 are installed in the first sub-case 410.

Referring to FIGS. 4 and 5, a 1-1st sub-inlet pipe 311-1, a 1-2nd sub-inlet pipe 311-2 and a first sub-outlet pipe 313 are respectively supported to the supporting block 110 so as to be protruded forward and backward. The 1-1st sub-inlet pipe 311-1 is to inject odorless air into the main body 1000, and the 1-2nd sub-inlet pipe 311-2 is to inject polluted gas into the main body 1000. Meanwhile, a protruded portion 110P is formed at a rear side of the supporting block 110. An insertion hole corresponding to the protruded portion 110P is formed in a rear surface of the first sub-case 410 so that the protruded portion 110P can be inserted therein so as to be protruded backward.

Referring to FIG. 4, a first connection pipe CP1 is connected to the 1-1st sub-inlet pipe 311-1, a second connection pipe CP2 is connected to the 1-2nd sub-inlet pipe 311-2, and a third connection pipe CP3 is connected to the first sub-outlet pipe 313. The third connection pipe CP3 is also connected with one of the first and second connection pipes CP1 and CP2 through the choice valve CV. An electric device for controlling the choice valve CV is installed at the valve controller 510. Further, a valve controller connector 510C is formed at the valve controller 510. The valve controller connector 510C is exposed to an outside through an opening hole (not designated by a reference numeral) formed in the rear surface of the first sub-case 410.

Referring to FIG. 6, a main block 120 and a main operation part 520 are installed at each main case 420.

Referring to FIG. 7, a main passage 120H is formed in the main block 120. The main passage 120H includes a first main passage 120H1, a second main passage 120H2 and a third main passage 120H3 which are communicated with each other. The first and third main passages 120H1 and 120H3 may be formed forward and backward, and the second main passage 120H2 may be formed upward and downward so as to communicate front ends of the first and third main passages 120H1 and 120H3 with each other.

Referring to FIG. 7, a gas concentration measuring sensor 220S which is contacted with gas flowed in the main passage 120H is installed at the main block 120. The gas concentration measuring sensor 220S may be a semiconductor type gas concentration measuring sensor, an electrochemical gas concentration measuring sensor, a photoionization type gas concentration measuring sensor or the like. The electrochemical gas concentration measuring sensor shows higher sensing efficiency when its sensing surface is arranged vertically with respect to a gas flow than when its sensing surface is arranged parallelly with the gas flow. Therefore, in case that the gas concentration measuring sensor 220S is the electrochemical gas concentration measuring sensor, the gas concentration measuring sensor 220S is disposed so that its sensing surface is arranged vertically with respect to a gas flow. To this end, the gas concentration measuring sensor 220S is disposed so that its sensing surface is arranged is located at a point that the first and second main passages 120H1 and 120H2 are connected with each other. Meanwhile, the man block 120 which is installed in a k-th main case 420-$k$ (referring to FIG. 1) is called a k-th main block 120, and the man block 120 which is installed in a (k+1)-th main case 420-($k$+1) (referring to FIG. 1) is called a (k+1)-th main block 120. Herein, k is a natural number from 1 to n−1. Further, the gas concentration measuring sensor 220S which are respectively installed at the k-th main block 120 and (k+1)-th main block 120 may be different from each other in order to sense the different pollutant components.

Referring to FIGS. 6 and 7, a main inlet pipe 321 and a main outlet pipe 323 are installed at the main block 120 so as to be protruded backward. The main inlet pipe 321 is disposed to be communicated with the first main passage 120H1, and the main outlet pipe 323 is disposed to be communicated with the third main passage 120H3. Meanwhile, a protruded portion 120P is formed at the main block 120 so as to be protruded backward. An insertion hole corresponding to the protruded portion 120P is formed in a rear surface of the main case 420 so that the protruded portion 120P can be inserted therein so as to be protruded backward.

Referring to FIG. 6, an electric device for calculating a concentration of the pollutant component is installed at the main operation part 520. Therefore, the main operation part 520 is connected to the gas concentration measuring sensor 220S so as to receive a signal detected by the gas concentration measuring sensor 220S. A method of calculating the concentration of the pollutant component using the main operation part 520 is detailedly disclosed in the "method for measuring concentration of gas and device for the same" (Korean Patent Application No. 10-2009-0100544). Further, a main operation part connector 520C is formed at the main operation part 520. The main operation part connector 520C is exposed to an outside through an opening hole (not designated by a reference numeral) formed in the rear surface of the main case 420.

Referring to FIG. 8, a sub-block 130 and a sub-operation part 530 are installed at the second sub-case 430.

Referring to FIG. 9, a sub-passage 130H is formed in the sub-block 130. The sub-passage 130H includes a first sub-passage 130H1, a second sub-passage 130H2 and a third sub-passage 130H3 which are communicated with each other. The first and third sub-passages 130H1 and 130H3 may be formed forward and backward, and the second sub-passage 130H2 may be formed upward and downward so as to communicate front ends of the first and third sub-passages 130H1 and 130H3 with each other.

Referring to FIG. 9, a physical property measuring sensor 230S which is contacted with gas flowed in the sub-passage 130H is installed at the sub-block 130. The physical property measuring sensor 230S may be a sensor for sensing at least one of temperature and humidity of gas flowed in the sub-passage 130H.

Referring to FIGS. 8 and 9, a second sub-inlet pipe 331 and a second sub-outlet pipe 333 are installed at the sub-block 130 so as to be protruded backward. The second sub-inlet pipe 331 is disposed to be communicated with the first sub-passage 130H1, and the second sub-outlet pipe 333 is disposed to be communicated with the third sub-passage 130H3. Meanwhile, a protruded portion 130P is formed at the sub-block 130 so as to be protruded backward. An insertion hole corresponding to the protruded portion 130P is formed in a rear surface of the sub-case 430 so that the protruded portion 130P can be inserted therein so as to be protruded backward.

Referring to FIG. 8, an electric device for calculating at least one of the temperature and humidity of gas flowed in the sub-passage 130H is installed at the sub-operation part 530. Therefore, the sub-operation part 530 is connected to the physical property sensor 230S so as to receive a signal detected by the physical property sensor 230S. Further, a sub-operation part connector 530C is formed at the sub-operation part 530. The sub-operation part connector 530C is exposed to an outside through an opening hole (not designated by a reference numeral) formed in the rear surface of the sub-case 430.

Referring to FIGS. 2 and 10, a 1-1st main body inlet hole 1111H1 and a 1-2nd main body inlet hole 1112H1 are formed in the rear surface of the main body 1000. Referring to FIGS. 1 and 4, the 1-1st main body inlet hole 1111H1 is formed so that the 1-1st sub-inlet pipe 311-1 is inserted therein when the first sub-case 410 is fitted into the receiving portion (not designated by a reference numeral) of the main body 1000. Referring to FIGS. 1 and 4, the 1-2nd main body inlet hole 1112H1 is formed so that the 1-2nd sub-inlet pipe 311-2 is inserted therein when the first sub-case 410 is fitted into the receiving portion (not designated by a reference numeral) of the main body 1000.

Referring to FIG. 10, a first sub-flow groove 1210G in which the gas is flowed is formed in the rear surface of the main body 1000. The first sub-flow groove 1210G is formed into a straight shape which is inclined at a desired angle with respect to a horizontal plane.

Referring to FIG. 10, a first sub-outlet hole 1210H3 is formed at an upper end of the first sub-flow groove 1210G and a first sub-inlet hole 1210H1 is formed at a lower end of the first sub-flow groove 1210G. Referring to FIGS. 1 and 2, the first sub-outlet hole 1210H3 is formed so that the first sub-outlet pipe 313 (referring to FIG. 4) is inserted therein when the first sub-case 410 is fitted into the receiving portion (not designated by a reference numeral) of the main body 1000. As the first sub-outlet pipe 313 (referring to FIG. 4) is inserted into the first sub-outlet hole 1210H3, the first sub-outlet pipe 313 (referring to FIG. 4) is communicated with the first sub-flow groove 1210G. Referring to FIGS. 1 and 2, the first sub-inlet hole 1210H1 is formed so that the main inlet pipe 321 (referring to FIG. 6) which is protruded toward a rear side of a first main case 420-1 is inserted therein when the first main case 420-1 is inserted into the receiving portion (not designated by a reference numeral) of the main body 1000. As the main inlet pipe 321 (referring to FIG. 6) which is protruded toward the rear side of the first main case 420-1 is inserted into the first sub-inlet hole 1210H1, the main inlet pipe 321 (referring to FIG. 6) which is protruded toward the rear side of the first main case 420-1 is communicated with the first sub-flow groove 1210G.

Referring to FIG. 10, an opening end of the first sub-flow groove 1210G is closed by a first sub-cover plate (not designated by a reference numeral). Therefore, the gas discharged through the first sub-outlet hole 1210H3 is flowed along the first sub-flow groove 1210G and then introduced into the first sub-inlet hole 1210H1. Meanwhile, the first sub-cover plate (not designated by a reference numeral) may be a part of a cover plate 1400. The cover plate 1400 is formed with a 1-1st cover plate inlet hole 1411H1 which exposes the 1-1st main body inlet hole 1111H1 to an outside, and a 1-2nd cover plate inlet hole 1412H1 which exposes the 1-2nd main body inlet hole 1112H1 to an outside.

Referring to FIG. 10, a first sub-insertion groove (not designated by a reference numeral) is formed in the rear surface of the main body 1000 so as to enclose the first sub-flow groove 1210G. A first sub-gasket 1210S is fitted into the first sub-insertion groove (not designated by a reference numeral). Because the first sub-gasket 1210S is fitted into the first sub-insertion groove (not designated by a reference numeral) and then pressed by the cover plate 1400, it is possible to increase an air-tightness with respective to the gas flowed in the first sub-flow groove 1210G.

That is, in one embodiment of the present invention, a first sub-connecting means for communicating and connecting the first sub-outlet pipe 313 and the main inlet pipe 321 which is protruded toward the rear side of the first main case 420-1 may be the first sub-cover plate (not designated by a reference numeral) and the main body 1000 in which the first sub-flow groove 1210G is formed. However, in other embodiment of the present invention, the first sub-connecting means may be a first sub-connection pipe of which one end is communicated with the first sub-outlet hole 1210H3 and the other end is communicated with the first sub-inlet hole 1210H1.

Referring to FIG. 10, n−1 main flow grooves 1220G in which the gas is flowed are formed in the rear surface of the main body 1000. Herein, since n is 9, eight main flow grooves 1220G are formed in the rear surface of the main body 1000. The eight main flow grooves 1220G are formed into a straight shape which is inclined at a desired angle with respect to a horizontal plane.

Referring to FIG. 10, a k-th main outlet hole 1220H3-$k$ is formed at an upper end of a k-th main flow groove 1220G-k and a k-th main inlet hole 1220H1-$k$ is formed at a lower end of the k-th main flow groove 1220G-k. Thus, a first main outlet hole 1220H3 is formed at an upper end of a first main flow groove 1220G-1 and a first main inlet hole 1220H1 is formed at a lower end of the first man flow groove 1220G. Likewise, a (n−1)-th main outlet hole 1220H3-($n$−1) is formed at an upper end of a (n−1)-th main flow groove 1220G-($n$−1) and a (n−1)-th main inlet hole 1220H1-($n$−1) is formed at a lower end of the (n−1)-th main flow groove 1220G-($n$−1). Referring to FIGS. 1 and 3, the k-th main outlet hole 1220H3-$k$ is formed so that the main outlet pipe 323 (referring to FIG. 6) which is protruded toward a rear side of a k-th main case 420-$k$ is inserted therein when the k-th main case 420-$k$ is inserted into the receiving portion (not designated by a reference numeral) of the main body 1000. As the main outlet pipe 323 (referring to FIG. 6) which is protruded toward the rear side of the k-th main case 420-$k$ is inserted into the k-th main outlet hole 1220H3-$k$, the main outlet pipe 323 (referring to FIG. 6) which is protruded toward the rear side of the k-th main case 420-$k$ is communicated with the k-th main flow groove 1220G-k. Referring to FIGS. 1 and 3, the k-th main inlet hole 1220H1-$k$ is formed so that the main inlet pipe 321 (referring to FIG. 6) which is protruded toward the rear side of the k-th main case 420-$k$ is inserted therein when the k-th main case 420-$k$ is inserted into the receiving portion (not designated by a reference numeral) of the main body 1000. As the main inlet pipe 321 (referring to FIG. 6) which is protruded toward the rear side of the k-th main case 420-$k$ is inserted into the k-th main inlet hole 1220H1-$k$, the main inlet pipe 321 (referring to FIG. 6) which is protruded toward the rear side of the k-th main case 420-$k$ is communicated with the k-th main flow groove 1220G-k.

Referring to FIG. 10, an opening end of the k-th main flow groove 1220G-k is closed by the k-th main cover plate (not designated by a reference numeral). Therefore, the gas discharged through the k-th main outlet hole 1220H3-$k$ is flowed along the k-th main flow groove 1220G-k and then introduced into the k-th main inlet hole 1220H1-$k$. Meanwhile, the k-th main cover plate (not designated by a reference numeral) may be a part of a cover plate 1400.

Referring to FIG. 10, a k-th main insertion groove (not designated by a reference numeral) is formed in the rear surface of the main body 1000 so as to enclose the k-th main flow groove 1220G-k. A k-th main gasket 1210S-k is fitted into the k-th main insertion groove (not designated by a reference numeral). Because the k-th main gasket 1210S-k is fitted into the k-th main insertion groove (not designated by a reference numeral) and then pressed by the cover plate 1400, it is possible to increase an air-tightness with respective to the gas flowed in the k-th main flow groove 1220G-k. A reference numeral 1210$s$-1 is a first main gasket, and a reference numeral 1210S-(n−1) is a (n−1)-th main gasket.

That is, in one embodiment of the present invention, a k-th main connecting means for communicating and connecting the main outlet pipe 323 protruded toward the rear side of the k-th main case 420-$k$ and the main inlet pipe 321 protruded toward a rear side of a (k+1)-th main case 420-($k$+1) may be the k-th main cover plate (not designated by a reference numeral) and the main body 1000 in which the k-th main flow groove 1220G-k is formed. However, in other embodiment of the present invention, the k-th main connecting means may be a k-th main connection pipe of which one end is communicated with the k-th main outlet hole 1220H3-$k$ and the other end is communicated with the k-th main inlet hole 1220H1-$k$.

Referring to FIG. 10, a second sub-flow groove 1230G in which the gas is flowed is formed in the rear surface of the main body 1000. The second sub-flow groove 1230G is formed into a straight shape which is inclined at a desired angle with respect to a horizontal plane.

Referring to FIG. 10, a second sub-outlet hole 1230H3 is formed at an upper end of the second sub-flow groove 1230G and a second sub-inlet hole 1230H1 is formed at a lower end of the second sub-flow groove 1230G. Referring to FIGS. 1 and 3, the second sub-outlet hole 1230H3 is formed so that the main outlet pipe 323 (referring to FIG. 6) which is protruded toward a rear side of an n-th main case 420-$n$ is inserted therein when the n-th main case 420-$n$ is fitted into the receiving portion (not designated by a reference numeral) of the main body 1000. As main outlet pipe 323 (referring to FIG. 6) which is protruded toward a rear side of an n-th main case 420-n is inserted into the second sub-outlet hole 1230H3, the main outlet pipe 323 (referring to FIG. 6) which is protruded toward a rear side of an n-th main case 420-n is inserted is communicated with the second sub-flow groove 1230G. Referring to FIGS. 1 and 3, the second sub-inlet hole 1230H1 is formed so that the second sub-inlet pipe 331 (referring to FIG. 8) is inserted therein when the second sub-case 430 is inserted into the receiving portion (not designated by a reference numeral) of the main body 1000. As the second sub-inlet pipe 331 (referring to FIG. 8) is inserted into the second sub-inlet hole 1230H1, the second sub-inlet pipe 331 (referring to FIG. 8) is communicated with the second sub-flow groove 1230G.

Referring to FIG. 10, an opening end of the second sub-flow groove 1230G is closed by a second sub-cover plate (not designated by a reference numeral). Therefore, the gas discharged through the second sub-outlet hole 1230H3 is flowed along the second sub-flow groove 1230G and then introduced into the second sub-inlet hole 1230H1. Meanwhile, the second sub-cover plate (not designated by a reference numeral) may be a part of a cover plate 1400.

Referring to FIG. 10, a second sub-insertion groove (not designated by a reference numeral) is formed in the rear surface of the main body 1000 so as to enclose the second sub-flow groove 1230G. A second sub-gasket 1230S is fitted into the second sub-insertion groove (not designated by a reference numeral). Because the second sub-gasket 1230S is fitted into the second sub-insertion groove (not designated by a reference numeral) and then pressed by the cover plate 1400, it is possible to increase an air-tightness with respective to the gas flowed in the second sub-flow groove 1230G.

That is, in one embodiment of the present invention, a second sub-connecting means for communicating and connecting the second sub-inlet pipe 331 and the main outlet pipe 323 which is protruded toward the rear side of the n-th main case 420-n may be the second sub-cover plate (not designated by a reference numeral) and the main body 1000 in which the second sub-flow groove 1230G is formed. However, in other embodiment of the present invention, the second sub-connecting means may be a second sub-connection pipe of which one end is communicated with the second sub-outlet hole 1230H3 and the other end is communicated with the second sub-inlet hole 1230H1.

Referring to FIGS. 3 and 10, a main body outlet hole 1300H3 is formed in the rear surface of the main body 1000. Referring to FIGS. 1 and 8, the main body outlet hole 1300H3 is formed so that the second sub-outlet pipe 333 is inserted therein when the second sub-case 430 is fitted into the receiving portion (not designated by a reference numeral) of the main body 1000. A cover plate outlet hole 1430H3 is formed in the cover plate 1400 so as to expose the main body outlet hole 1300H3 to an outside.

Referring to FIG. 1, a display part 1500 is installed at the main body 1000. The display part 1500 functions to display the concentration of the pollutant component calculated from the main operation part 520 and the temperature or the humidity calculated from the sub-operation part 530. Meanwhile, the display part 1500 may be a touch screen which can apply an input signal for controlling the valve controller 510 or the main operation part 520. By applying a specific input signal to the touch screen, the choice valve CV allows the third connection pipe CP3 to be connected with one of the first and second connection pipes CP1 and CP2.

Referring to FIGS. 2 and 3, a display part connector 1500C connected to the display part 1500 is installed in the receiving portion of the main body 1000. The display part connector 1500C includes a first sub-display part connector 1510C, n main display part connectors 1520C and a second sub-display part connector 1530C. The first sub-display part connector 1510C is disposed to be connected with the valve controller connector 510C when the first sub-case 410 is fitted into the receiving portion of the main body 1000. The n main display part connectors 1520C are disposed so as to be respectively connected with each of the n main operation part connectors 520C when the n main cases 420 are fitted into the receiving portion of the main body 1000. The second sub-display part connector 1530C is disposed so as to be connected with the sub-operation part connector 530C when the second sub-case 430 is fitted into the receiving portion of the main body 1000.

In the one embodiment of the present invention, the main operation part 520 and gas concentration measuring sensor 120S for sensing a specific pollutant component and concentration are installed at a single main case 420-k, thereby forming a single measurement unit. Further, one measurement unit is connected with another measurement unit through the main connecting means so that the gas passing through the one measurement unit can pass, in turn, through another measurement. In this case, the measurement units are simply fitted into the receiving portion (not designated by a reference numeral) of the main body 1000 and thus connected with each other through the main connecting means. Therefore, when it is necessary to exchange a specific gas concentration measuring sensor 120S or mean operation part 520, a measurement unit having the specific gas concentration measuring sensor or main operation part is separated from the receiving portion of the main body and then exchanged with other equivalent measurement unit, thereby facilitating sensor exchange.

While the present invention has been described with respect to the specific embodiments, it will be apparent to those skilled in the art that various changes and modifications may be made without departing from the spirit and scope of the invention as defined in the following claims.

What is claimed is:

1. A pollution measurement apparatus for easily exchanging a sensor, comprising:
    a main block in which a main passage is formed and also a gas concentration measuring sensor contacted with gas flowed in the main passage is installed;
    a main case in which the main block and a main operation part connected with the gas concentration measuring sensor are installed;
    a main inlet pipe which is protruded toward a rear side of the main case so as to be communicated with the main passage;
    a main outlet pipe which is protruded toward the rear side of the main case so as to be communicated with the main passage;
    a main body which is formed with a receiving portion that n main cases are fitted therein through a front surface thereof; and
    a k-th main connecting means which connects and communicates the main outlet pipe protruded toward a rear side of a k-th main case out of the n main cases and the main inlet pipe protruded toward a rear side of a (k+1)-th main case out of the n main cases with each other,
    wherein (n−1) main flow grooves through which the gas is flowed are formed in a rear surface of the main body,
    a k-th main flow groove out of the (n−1) main flow grooves is formed with a k-th main outlet hole in which the main outlet pipe protruded toward the rear side of the k-th main case is inserted so as to be communicated with the k-th main flow groove, and a k-th main inlet hole in which the main inlet pipe protruded toward the rear side of the (k+1)-th main case is inserted so as to be communicated with the k-th main flow groove, and the k-th main connecting means comprises a k-th main cover plate which is installed at the rear surface of the main body so as to air-tightly close an opening end of the k-th main flow groove, and wherein n is a natural number more than 2 and k is a natural number from 1 to n−1.

2. The pollution measurement apparatus according to claim 1, further comprising:

a first sub-case which is fitted into the receiving portion of the main body and in which a first sub-inlet pipe for injecting odorless air, a second sub-inlet pipe for injecting polluted gas and a first sub-outlet pipe are respectively protruded backward, and a choice valve is installed so as to selectively connect one of the first sub-inlet pipe and the second sub-inlet pipe with the first sub-outlet pipe; and a first sub-connecting means which communicates and connects the first sub-outlet pipe with the main inlet pipe protruded toward a rear side of a first main case out of the n main cases.

3. The pollution measurement apparatus according to claim 2, wherein a first sub-flow groove through which the gas is flowed is formed in the rear surface of the main body, the first sub-flow groove is formed with a first sub-outlet hole in which the first sub-outlet pipe is inserted so as to be communicated with the first sub-flow groove, and a first sub-inlet hole in which the main inlet pipe protruded toward the rear side of the first main case is inserted so as to be communicated with the first sub-flow groove, and the first sub-connecting means comprises a first sub-cover plate which is installed at the rear surface of the main body so as to air-tightly close an opening end of the first sub-flow groove.

4. The pollution measurement apparatus according to claim 3, wherein the rear surface of the main body is formed with a first main body inlet hole in which the first sub-inlet pipe is inserted and a second main body inlet hole in which the second sub-inlet pipe is inserted.

5. The pollution measurement apparatus according to claim 1, further comprising:

a sub-block in which a sub-passage is formed, and a physical property measuring sensor for sensing at least one of temperature and humidity of the gas flowed in the sub-passage is installed;

a second sub-case which is fitted into the receiving portion of the main body and in which the sub-block and a sub-operation part connected with the physical property measuring sensor are installed;

a second sub-inlet pipe which is protruded toward a rear side of the sub-case so as to be communicated with the sub-passage;

a second sub-outlet pipe which is protruded toward the rear side of the sub-case so as to be communicated with the sub-passage; and a second sub-connecting means which communicates and connects the second sub-inlet pipe with the main outlet pipe protruded toward a rear side of an n-th main case out of the n main cases.

6. The pollution measurement apparatus according to claim 5, wherein a second sub-flow groove through which the gas is flowed is formed in the rear surface of the main body, the second sub-flow groove is formed with a second sub-outlet hole in which the main outlet pipe protruded toward the rear side of the n-th main case is inserted so as to be communicated with the second sub-flow groove, and a second sub-inlet hole in which the second sub-inlet pipe is inserted so as to be communicated with the second sub-flow groove, and the second sub-connecting means comprises a second sub-cover plate which is installed at the rear surface of the main body so as to air-tightly close an opening end of the second sub-flow groove.

7. The pollution measurement apparatus according to claim 6, wherein the rear surface of the main body is formed with a main body outlet hole in which the second sub-outlet pipe is inserted.

8. The pollution measurement apparatus according to claim 1, wherein a display part for displaying a concentration of a pollutant component is installed at the main body, a main display part connector connected with the display part is installed in the receiving part of the main body, and the main operation part is provided with a main operation part connector which is fitted into the main display part connector when the main case is fitted into the receiving portion of the main body.

* * * * *